United States Patent
Habenstein et al.

[11] Patent Number: 5,756,359
[45] Date of Patent: May 26, 1998

[54] DECREASED INTERFERENCE REDOX DETECTION SYSTEM

[75] Inventors: Klaus Habenstein, Wetter; Dieter Zopf; Winfried Bursch, both of Marburg, all of Germany

[73] Assignee: Behring Diagnostics GmbH, Marburg, Germany

[21] Appl. No.: 859,083

[22] Filed: May 20, 1997

Related U.S. Application Data

[62] Division of Ser. No. 605,746, Feb. 22, 1996, Pat. No. 5,683,656.

[30] Foreign Application Priority Data

Feb. 23, 1995 [DE] Germany .................. 195 06 262.0

[51] Int. Cl.$^6$ ............................................. G01N 33/48
[52] U.S. Cl. ..................... 436/166; 436/169; 436/95; 436/99; 422/56
[58] Field of Search ............... 422/56–57; 436/169–170, 436/95, 99, 166

[56] References Cited

U.S. PATENT DOCUMENTS

| | | |
|---|---|---|
| 3,411,887 | 11/1968 | Ku et al. . |
| 3,904,481 | 9/1975 | LaRue et al. .................. 195/103.5 |
| 4,910,135 | 3/1990 | Tischer et al. ..................... 435/28 |

FOREIGN PATENT DOCUMENTS

| | | |
|---|---|---|
| 0041188A2 | 12/1981 | European Pat. Off. . |
| 0103958A1 | 3/1984 | European Pat. Off. . |
| 0123115A1 | 10/1984 | European Pat. Off. . |
| 0141244A1 | 5/1985 | European Pat. Off. . |
| 0480340A1 | 4/1992 | European Pat. Off. . |
| 0513594A2 | 11/1992 | European Pat. Off. . |

OTHER PUBLICATIONS

Andrew C. Dengel et al., "Tetraphenylphosphonium perosmate (VII) as an oxidant: comparison of [OsO$_4$]–with [RuO$_4$]–", Transition Met. Chem., 14 pp. 230–232 (1989).

Toshikazu Takata et al., "Mild and Selective Oxygen Atom Transfer: "Bu$_4$NIO$_4$ With Metalloporphyrins," Tetrahedron Letters, vol. 24, No. 34, pp. 3631–3634 (1983).

*Primary Examiner*—Lyle A. Alexander
*Attorney, Agent, or Firm*—Finnegan, Henderson, Farabow, Garrett & Dunner, L.L.P.

[57] ABSTRACT

The present invention relates to reagents and processes for the preparation of diagnostics which use a chromogenic redox detection system and whose chromogenic redox detection system essentially remains unaffected by interference from reducing. compounds in the sample material.

11 Claims, No Drawings

DECREASED INTERFERENCE REDOX DETECTION SYSTEM

This is a division of application Ser. No. 08/605,746, filed Feb. 22, 1996, now U.S. Pat. No. 5,683,656.

The present invention relates to reagents and processes for the preparation of diagnostics which use a chromogenic redox detection system and whose chromogenic redox detection system essentially remains unaffected by interference from reducing compounds in the sample material.

Redox detection systems of this type are employed both in wet-chemical and in so-called dry-chemical test methods.

In particular, detection systems are employed here in which the detection is performed using a redox chair. This can consist of an oxidase which reacts with the analyte with release of $H_2O_2$, a peroxidase as an electron carrier and a redox indicator as an electron donor. However, it can also be formed from an analyte having electron carrying properties (pseudoperoxidase), a strong oxidant and the redox indicator as electron donor.

Dry-chemical test systems as such are known to the person skilled in the art.

Owing to the system, redox-active substances, in particular reducing compounds, interfere with these detection systems.

Several processes have been described which remove interfering sample constituents from the sample material with the aid of oxidizing media before carrying out analyses:

The oxidants employed here are, for example, ascorbate oxidase (EP-A 0 016 962), heavy metal salts (US 3,411,887), transition metals (EP-A 0 041 188), iron complexes (EP-A 0 123 115) or periodates (EP-A 0 103 958).

Ascorbate oxidase acts very sluggishly and is thus less suitable, in particular for a "dry-chemical" rapid test. The heavy metals mentioned mostly have intensive intrinsic colors, which moreover distinctly change on reaction with ascorbic acid, such that the actual chromogenic detection reaction is difficult to detect.

Periodates can be impregnated in papers, but enter into a quantitative reaction with the cellulose to give carbohydrate aldehydes and iodate.

Iodate reacts with the chromogens customarily used in a slow reaction which, on test papers, leads to an intrinsic coloration during the test phase (i.e. false-positive color indication). This can be solved by expensive overlaying of several test papers (EP-A 0 037 056), whereby iodate and indicator dye are spatially separated from one another.

The insoluble oxidation compounds in general belong to the abovementioned heavy metal compounds having a strong intrinsic color. Moreover, these compounds also oxidize the indicator dyes used with a false-positive color indication.

The iron complex compounds (EP-A 0 123 115) require a further oxidant for the oxidation to a higher state of the iron salt reduced by the reductant (for example ascorbic acid), as is described in EP-A 0 513 594.

Although the solutions according to the prior art also already provided a certain advantage, there was nevertheless a need for a redox detection system which essentially remains unaffected by reducing constituents of a sample.

The present invention was thus based on the technical problem of finding reagents which, in a redox detection system, prevent interference from reducing substances and at the same time leave the chromogenic substances used, or the colored substances formed from them, unaffected, or even stabilize them.

This technical problem was solved by the provision of the embodiments described in the patent claims.

It was surprisingly realized that the solution had been found by complexation of the periodate ion known to have an extremely oxidizing action, suitable complexing agents for the periodate ion being substances of the following formula I

$$[Z(R_n)]^{(+)}A^{(-)} \qquad (I)$$

in which

Z=P, N, As, S or Se, n=4 if Z=P, N or As and 3 if Z=S or Se

R=phenyl, benzyl, alkyl or cycloalkyl which can each also be substituted by C 1–8-alkyl and $A^{(-)}=Br^{(-)}$, $I^{(-)}$, $Cl^{(-)}$ or $F^{(-)}$, preferably Z=P, N or As and R=phenyl, benzyl, cycloalkyl, each of which can also be substituted by C 1–8-alkyl, and alkyl, particularly preferably Z=P, N or As and R=phenyl, benzyl, cycloalkyl or alkyl, where the sum of the C atoms should be greater than 12 if R only consists of alkyl radicals, very preferably R=phenyl, benzyl, alkyl or cycloalkyl, each of which can also be substituted by C 1–4 alkyl.

These react with periodate to give the complex of the formula II

$$R_nZ\ IO_4 \text{ for S or Se} \qquad (II)$$

in which R, n and Z have the abovementioned meaning.

The complexes described here have reduced solubility in water, but dissolve well in certain organic solvents.

The stabilization of the oxidation potential according to the invention is seen in the fact that the complexes, in contrast to the free periodate, react neither with the cellulose fibers of the paper (during impregnation) nor with oxidation indicators in the presence of the stabilizers customarily used in the preparation of test papers.

A preferred embodiment of the test paper according to the invention is prepared in the following manner:

a) 1–10 g of a polybasic carboxylic acid having a $pK_a$ of approximately 4 to 6-citric acid, tricarballylic acid, phthalic acid, maleic acid and glutaric acid are particularly preferred here - are dissolved in 50 ml of $H_2O$ and the pH is adjusted to 4.5–5.5, preferably to approximately 5.

b) 0.1–1 g of a gel- and/or film-forming substance, for example gelatin, polygeline, Mowiol®, Mowilith®, Gantrez®, cellulose esters and/or ethers and povima 10–200 mg of a complexing agent, for example EDTA, 10–200 mg of a background dye, for example tartrazine and 1–10 mg of an enzyme inhibitor and antioxidant, for example hydroquinone, tin chloride, aminonaphthalenesulfonic acid or ascorbic acid, is dissolved in 20 ml of $H_2O$ and made up to 60 ml using the buffer prepared in a).

50–200 mg each of glucose oxidase and peroxidase, advantageously in a weight ratio of approximately 1:1, are dissolved in 7 ml of the buffer prepared in a) and added to the solution (60 ml) prepared in b). Periodate-containing papers, for example those prepared in Example 2, are impregnated with this solution and dried at a suitable temperature. The test elements thus obtained which advantageously can also consist of synthetic carriers, for example membranes, which are impregnated with periodate-containing solution by the process according to the invention - are then impregnated with a solution of 10–100 mg of a peroxidase substrate, such as tetramethylbenzidine, in 10 ml of an organic solvent, such as toluene. The test element thus obtained is dried in a suitable manner.

The following examples illustrate the invention.

As is shown in the examples, the abovementioned compounds can be impregnated in paper without decomposition, which is not possible with free periodate.

EXAMPLE 1

Preparation of benzyltriphenylphosphorium periodate (BTPP)

Solution 1: 5 g of sodium periodate in 250 ml of deionized water

Solution 2: 5 g of benzyltriphenylphosphonium chloride in 500 ml of deionized water Solution 2 is added dropwise to solution 1 in the course of 10 min with stirring. The mixture is stirred for a further 5 min and then allowed to stand for 10 min. The precipitate is filtered off, resuspended in 200 ml of deionized water and dried after filtering again.

Yield: 6.6 g of benzyltriphenylphosphonium periodate

The following complex compounds can be prepared in an analogous manner:

Cyclohexyltriphenylphosphonium periodate, benzethonium periodate, hexadecyltrimethylammonium periodate, dodecylpyridinium periodate, tetradodecylammonium periodate, tetraphenylarsonium periodate and ethoxycarbonylmethyldimethylsulphonium periodate.

In the case of the more strongly hydrophobic compounds of this series, solution 2 is advantageously prepared using an ethanol/water mixture.

EXAMPLE 2

Impregnation of benzyltriphenylphosponium periodate (BTPP) in paper:

A) Impregnation with organic/aqueous solution:

Untreated indicator paper SS2316 from Schleicher and Schüll is immersed for approximately 2 min in an impregnating dish containing a 1% solution of BTPP in acetone/water (6+4), the excess of impregnating solution is stripped off between two glass rods and the paper is dried for 5 min at 80° C. in a recirculating air drying oven.

The following compounds can be detected on the paper thus prepared, after washing with deionized water:

$IO^-_4$: 58 µg/cm$^2$

B) Direct precipitation:

Solution 1: 10 g of benzyltriphenylphosphonium chloride are dissolved in 1000 ml of deionized water.

Solution 2: 5 g of sodium periodate are dissolved in 1000 ml of deionized water.

Untreated indicator paper T86 from J. C. Binzer is treated successively with solution 1 and solution 2 as described in A. The following compounds can be detected on the paper thus prepared, after washing with deionized water:

$IO^-_4$: 44 µg/cm$^2$

If the sequence of the impregnating solutions is exchanged, the previously described, substantial reaction of the periodate with the cellulose with formation of iodate takes place during the impregnation of the periodate solution. The residual amount of periodate reacts with the phosphonium chloride with formation of the very poorly soluble BTPP and can subsequently still be detected on the paper after washing:

$IO^-_4$: 10 µg/cm$^2$

In contrast to BTPP, iodate is readily water-soluble and can easily be removed from, the paper by washing, as the following experiment shows:

Solution 1: 10 g of benzyltriphenylphosphonium chloride are dissolved in 1000 ml of deionized water.

Solution 2: 5 g of sodium iodate are dissolved in 1000 ml of deionized water.

Untreated indicator paper T86 from J. C. Binzer is treated successively with solution 1 and solution 2 as described in B.

On the paper thus prepared, after washing with deionized water $IO^-_3$ can no longer be detected.

The other compounds mentioned in Example 1 have analogous behavior.

EXAMPLE 3

Preparation of a test paper for the detection of glucose in sample fluids 7 g of sodium citrate are dissolved in 50 ml of deionized water and the pH is adjusted to pH 5. 0.3 g of gelatin, 70 mg of EDTA, 50 mg of tartrazine and, 2 mg of hydroquinone are dissolved in 20 ml of deionized water. This solution is then made up to 60 ml with the citrate buffer. 100 mg each of glucose oxidase and peroxidase are dissolved in 7 ml of the citrate buffer and added to the above 60 ml. Periodate-containing papers (prepared according to Example 2) are impregnated with this reagent solution and dried at 50° C. in a recirculating air drying oven. The papers are then immersed in a solution of 30 mg of tetramethylbenzidine in 10 ml of toluene and the impregnated paper is again dried in a recirculating air drying oven at 50° C.

On immersing in a sample fluid containing 1 g of glucose and 2 g of ascorbic acid per liter, the glucose test paper thus obtained gives a green color indication. In comparison, no color indication is obtained using a test paper without the periodate complex according to the invention.

We claim:

1. A reagent for use with a redox detection system, which comprises periodate ions and a complexing agent of the formula I $$\{Z(R_n)\}^{(+)} A^{(-)} \qquad (I)$$

in which

Z is P, N, As, S or Se, n is 4 when Z is P, N or As and n is 3 when Z is S or Se, R is phenyl, benzyl, alkyl or cycloalkyl, each of which is unsubstituted or is substituted by C 1–8 alkyl, and $A^{(-)}$ is $Br^{(-)}$, $I^{(-)}$, $Cl^{(-)}$ or $F^{(-)}$.

2. A reagent as claimed in claim 1, in which

Z is P, N or As, and

R is phenyl, benzyl, cycloalkyl, each of which is unsubstituted or is substituted by C 1–8 alkyl or R is alkyl.

3. A reagent as claimed in claim 1, in which

Z is P, N or As, and

R is phenyl, benzyl, cycloalkyl or alkyl, where the sum of the C atoms is greater than 12 when R is alkyl.

4. A reagent as claimed in claim 1, in which

R is phenyl, benzyl, alkyl or cycloalkyl, each of which is unsubstituted or is substituted by C 1–4 alkyl.

5. A reagent as claimed in claim 1, wherein the reagent and the redox detection system are applied to a reagent support customary in a dry-chemical detection system.

6. A reagent as claimed in claim 5, wherein the reagent support is an indicator paper.

7. A diagnostic process for the detection and determination of an analyte in a sample of a biological fluid, which comprises conducting a redox detection reaction in the presence of a reagent which comprises periodate ions and a complexing agent of the formula I $$\{Z(R_n)\}^{(+)} A^{(-)} \qquad (I)$$

in which

Z is P, N, As, S or Se, n is 4 when Z is P, N or As and n is 3 when Z is S or Se, R is phenyl, benzyl, alkyl or cycloalkyl, each of which is unsubstituted or is substituted by C 1–8 alkyl, and $$A^{(-)} \text{ is } Br^{(-)}, I^{(-)}, Cl^{(-)} \text{ or } F^{(-)}.$$

8. A diagnostic process as claimed in claim 7, wherein the analyte is selected from the group consisting of glucose, uric acid, peroxidase and pseudoperoxidase.

9. A diagnostic process as claimed in claim 7, wherein said reagent is contacted with said sample of a biological fluid.

10. A diagnostic process as claimed in claim 7, wherein the reagent is applied to a reagent support.

11. A diagnostic process as claimed in claim 10, wherein the reagent support is an indicator paper.

* * * * *